(12) United States Patent
Pereira et al.

(10) Patent No.: US 8,558,017 B2
(45) Date of Patent: *Oct. 15, 2013

(54) RUTHENIUM (II) CATALYSTS FOR USE IN STEREOSELECTIVE CYCLOPROPANATIONS

(75) Inventors: David E. Pereira, Apex, NC (US); Wade Aumiller, Durham, NC (US); Raymond Dagger, Raleigh, NC (US)

(73) Assignee: Vanda Pharmaceuticals, Inc., Washington, DC (US)

( * ) Notice: Subject to any disclaimer, the term of this patent is extended or adjusted under 35 U.S.C. 154(b) by 156 days.

This patent is subject to a terminal disclaimer.

(21) Appl. No.: 13/316,729

(22) Filed: Dec. 12, 2011

(65) Prior Publication Data

US 2012/0149906 A1  Jun. 14, 2012
US 2013/0023662 A9  Jan. 24, 2013

Related U.S. Application Data

(60) Continuation of application No. 12/783,935, filed on May 20, 2010, now Pat. No. 8,097,738, which is a division of application No. 11/437,013, filed on May 18, 2006, now Pat. No. 7,754,902.

(51) Int. Cl.
*C07D 307/87* (2006.01)
*C07C 2/42* (2006.01)
*C07F 15/00* (2006.01)

(52) U.S. Cl.
USPC .............................. 549/462; 556/32; 585/368

(58) Field of Classification Search
USPC .............................. 549/462; 556/32; 585/368
See application file for complete search history.

(56) References Cited

U.S. PATENT DOCUMENTS 7,754,902 B2 *   7/2010   Pereira et al. .................. 549/462
8,097,738 B2 *   1/2012   Pereira et al. .................. 549/462
2007/0270593 A1 * 11/2007  Pereira et al. .................. 548/400

OTHER PUBLICATIONS

"Catalyst Development Update", Jan. 6, 2006, 7 pages, Report by Cardinal Health to Vanda Pharmaceuticals.*
U.S. Appl. No. 11/437,013, filed May 18, 2006, Notice of Allowance and Fees Due dated Feb. 25, 2010, 6 pages.
Kosack, Office Action Communication for U.S. Appl. No. 12/783,935 dated Aug. 30, 2010, 10 pages.
U.S. Appl. No. 11/437,013, filed May 18, 2006, Final Office Action dated Aug. 10, 2009, 10 pages.
Kosack, Office Action Communication for U.S. Appl. No. 12/783,935 dated May 23, 2011, 7 pages.
U.S. Appl. No. 11/437,013, filed May 18, 2006, Office Action dated Jan. 27, 2009, 7 pages.
Kosack, Notice of Allowance and Fees Due for U.S. Appl. No. 12/783,935 dated Sep. 13, 2011, 7 pages.
Miller et al., "An Efficient and Highly Enantio-and Diastereoselective Cyclopropanation of Olefins Catalyzed by Schiff-Base Ruthenium(II) Complexes", Angewandte Chemie. Int.ernational Edition, 2002, vol. 41, No. 16., pp. 2953-2956.
Nishiyama, Hisao, "Cyclopropanation with Ruthenium Catalysts", Topics in Organometallic Chemistry, 2004, vol. 11, pp. 81-92.

* cited by examiner

*Primary Examiner* — Joseph Kosack
(74) *Attorney, Agent, or Firm* — Stephen F. Swinton, Jr.; Hoffman Warnick LLC

(57) ABSTRACT

Chiral ruthenium catalysts comprising salen and alkenyl ligands are provided for stereoselective cyclopropanation, and methods of cyclopropanation are provided. The chiral ruthenium catalyst is prepared in situ by combining an alkenyl ligand, a deprotonated chiral salen ligand, and a ruthenium (II) metal. A preferred catalyst is prepared in situ by combining 2,3-dihydro-4-venylbenzofuran,deprotonated 1,2-cyclohexanediamino-N,N'-bis(3,5-di-t-butyl-salicylidene) and $RuCl_2$(p-cymene)]$_2$.

16 Claims, No Drawings

US 8,558,017 B2

RUTHENIUM (II) CATALYSTS FOR USE IN STEREOSELECTIVE CYCLOPROPANATIONS

CROSS-REFERENCE TO RELATED APPLICATIONS

This application is a continuation application of U.S. patent application Ser. No. 12/783,935, now U.S. Pat. No. 8,097,738, filed 20 May 2010, which is a divisional application of U.S. patent application Ser. No. 11/437,013, now U.S. Pat. No. 7,754,902, filed 18 May 2006, to each of which this application claims the benefit of priority.

TECHNICAL FIELD

Chiral catalysts for cyclopropanation, methods of preparation and methods of forming chiral cyclopropyl products are provided herein.

BACKGROUND

The biological activities of many pharmaceuticals, fragrances, food additives and agrochemicals are often associated with their absolute molecular configuration. While one enantiomer gives a desired biological function through interactions with natural binding sites, another enantiomer usually does not have the same function and sometimes has deleterious side effects. As such, chemical synthesis of biologically active compounds are usually directed at the desired enantiomerically pure form.

Cyclopropanes are particularly challenging to synthesize enantiomerically pure. Especially for commercial applications, stereoselective cyclopropanations must give good diastereo- and enantioselectivity in high yield and purity at a reasonable cost. One approach that is particularly efficient, is stereoselective catalysis because a small amount of a chiral catalyst can be used to produce a large quantity of the desired chiral cyclopropyl compound. Transition metal catalysts are typically employed to catalyze the reaction between a diazoester and an olefin substrate to form a chiral cyclopropyl product.

Current stereoselective cyclopropanation methods using transition metal catalysis, are nonoptimal for commercialization due to the use of a large excess olefin substrate or diazoester in order to drive the reaction to completion. Miller et el. (*Angew. Chem Int Ed.* 2002, 41, 2953-2956) report an isolated ruthenium catalyst formed from a chiral salen ligand and pyridine or phosphine ligands. The stereoselective cyclopropanation method of Miller et al. employs an isolated chiral ruthenium catalyst and five equivalents of the olefin substrate relative to the amount of diazoester employed. In commercial applications, the olefin substrates are often complex and require multi-step syntheses. As a result, using an excess of the olefin substrate not only wastes material, but also increases cost and lowers the throughput of the chemical process. On the other hand, using a large excess of the diazoester to drive the reaction to completion is undesirable due to safety concerns on large scale. Furthermore, use of excess reagents can lead to increased impurities and purification difficulties. Finally, the use of an isolated chiral catalyst can be undesirable in commercial applications because of the increased number of steps in a chemical process, increasing cycle time, as well as safety issues associated with handling transition metal catalysts. What is needed, are efficient transition metal catalyzed stereoselective cyclopropanation methods employing mild and safe conditions.

SUMMARY OF THE INVENTION

In one embodiment, a method of stereoselective cyclopropanation is provided. The stereoselective cyclopropanation reaction comprises combining a carbene precursor and an alkenyl substrate in the presence of a chiral catalyst to form a cyclopropyl product. The chiral catalyst is formed in situ by combining an alkenyl ligand with a deprotonated chiral ligand and a ruthenium (II) metal.

In another embodiment, a catalyst for stereoselective reactions is provided. The catalyst is prepared in situ by combining an alkenyl ligand and a deprotonated chiral ligand in the presence of a ruthenium (II) metal. The alkenyl ligand is of formula (I):

and the deprotonated ligand is of formula (III):

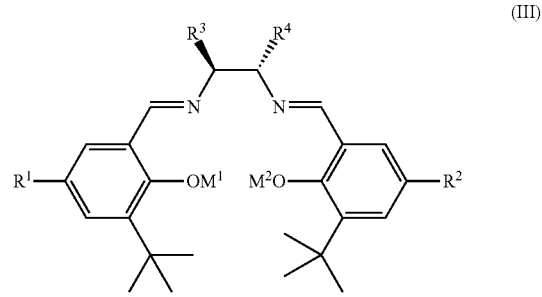

where $R^1$, $R^2$, $R^3$, $R^4$, $R^5$, $R^6$, $M^1$ and $M^2$ are defined below.

Thus, there is disclosed a method of stereoselective cyclopropanation comprising the step of combining a carbene precursor and an alkenyl substrate in the presence of a chiral catalyst to form a cyclopropyl product, the chiral catalyst is prepared in situ by the step of combining an alkenyl ligand and a deprotonated chiral ligand in the presence of a ruthenium (II) metal; wherein the alkenyl ligand is of formula (I):

where $R^5$ is selected from the group consisting of hydrogen, $C_{1-8}$ alkyl, $C_{6-10}$ aryl, $C_{5-10}$ heteroaryl, $C_{3-10}$ heterocycle; and where $R^6$ is selected from the group consisting of hydrogen, and $C_{1-8}$ alkyl; and where $R^5$ and $R^6$ together with the atoms to which they are attached may form a carbocyclic ring; wherein the deprotonated chiral ligand is of formula (III):

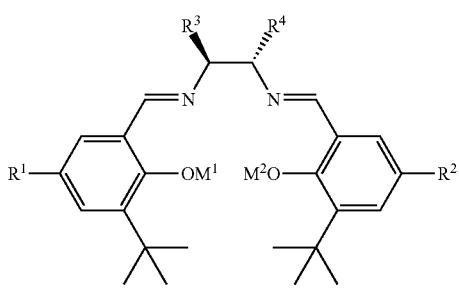

where $R^1$ and $R^2$ are each independently selected from the group consisting of hydrogen, substituted or unsubstituted $C_{1-8}$ alkyl, substituted or unsubstituted $C_{6-10}$ aryl, substituted or unsubstituted $C_{3-10}$ heterocyclyl, substituted or unsubstituted $C_{5-10}$ heteroaryl; where $R^3$ and $R^4$ are each independently selected from the group consisting of substituted or unsubstituted $C_{1-8}$ alkyl, substituted or unsubstituted $C_{3-8}$ cycloalkyl, $C_{1-10}$ alkoxy, $C_{1-12}$ alkylamino, substituted or unsubstituted $C_{3-10}$ heterocyclyl, substituted or unsubstituted $C_{6-10}$ aryl, substituted or unsubstituted $C_{5-10}$ heteroaryl and substituted or unsubstituted arylalkyl; where $R^3$ and $R^4$ together with the atoms to which they are attached may form a ring; and where $M^1$ and $M^2$ are each a counterion independently selected from the group consisting of Group I metal ions and Group II metal ions.

There is further disclosed a method of stereoselective cyclopropanation consisting of the steps of combining an alkenyl ligand and a deprotonated chiral ligand in the presence of a ruthenium (II) metal to form a chiral catalyst in situ; wherein the alkenyl ligand is of formula (I):

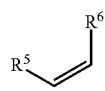

where $R^5$ is selected from the group consisting of hydrogen, $C_{1-8}$ alkyl, $C_{6-10}$ aryl, $C_{5-10}$ heteroaryl, $C_{3-10}$ heterocycle; and where $R^6$ is selected from the group consisting of hydrogen, and $C_{1-6}$ alkyl; and where $R^5$ and $R^6$ together with the atoms to which they are attached may form a carbocyclic ring; wherein the deprotonated chiral ligand is of formula (III):

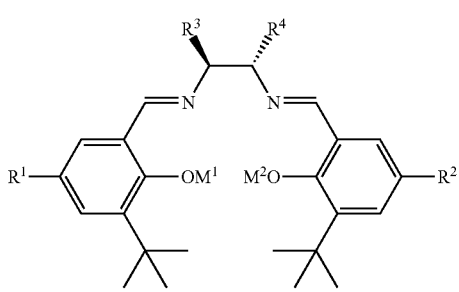

where $R^1$ and $R^2$ are each independently selected from the group consisting of hydrogen, substituted or unsubstituted $C_{1-6}$ alkyl, substituted or unsubstituted $C_{6-10}$ aryl, substituted or unsubstituted $C_{3-10}$ heterocyclyl, substituted or unsubstituted $C_{5-10}$ heteroaryl; where $R^3$ and $R^4$ are each independently selected from the group consisting of substituted or unsubstituted $C_{1-8}$ alkyl, substituted or unsubstituted $C_{3-8}$ cycloalkyl, $C_{1-10}$ alkoxy, $C_{1-12}$ alkylamino, substituted or unsubstituted $C_{10}$ heterocyclyl, substituted or unsubstituted $C_{6-10}$ aryl, substituted or unsubstituted $C_{5-10}$ heteroaryl and substituted or unsubstituted arylalkyl; where $R^3$ and $R^4$ together with the atoms to which they are attached may form a ring; and where $M^1$ and $M^2$ are each a counterion independently selected from the group consisting of Group I metal ions and Group II metal ions; and combining a carbene precursor and an alkenyl substrate in the presence of the chiral catalyst to form a cyclopropyl product.

Also disclosed is the stereoselective cyclopropanation of a carbene precursor and an alkenyl substrate with a chiral catalyst of the formulae (V) or (VI):

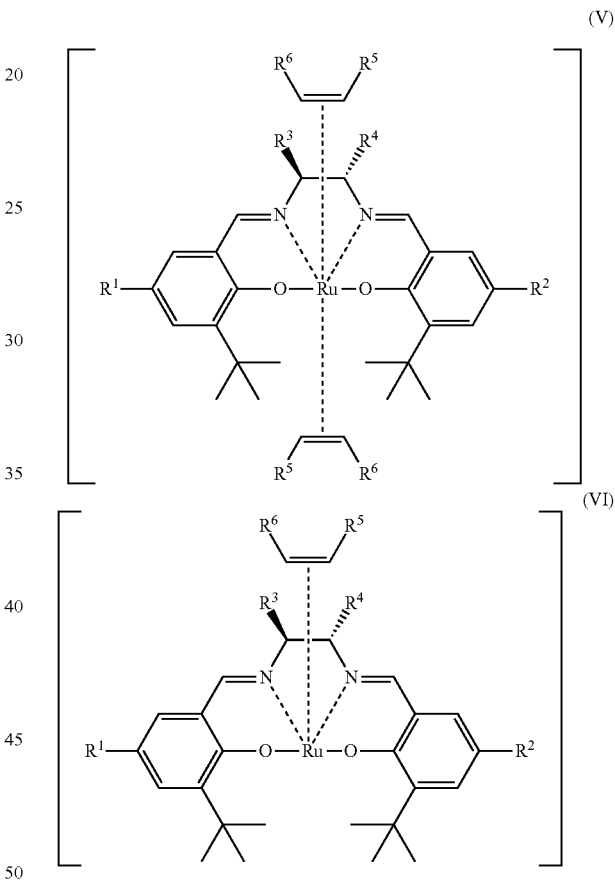

where $R^5$ is selected from the group consisting of hydrogen, $C_{1-8}$ alkyl, $C_{6-10}$ aryl, $C_{5-10}$ heteroaryl, $C_{3-10}$ heterocycle; and where $R^6$ is selected from the group consisting of hydrogen, and $C_{1-6}$ alkyl; and where $R^5$ and $R^6$ together with the atoms to which they are attached may form a carbocyclic ring; where $R^1$ and $R^2$ are each independently selected from the group consisting of hydrogen, substituted or unsubstituted $C_{1-8}$ alkyl, substituted or unsubstituted $C_{6-10}$ aryl, substituted or unsubstituted $C_{3-10}$ heterocyclyl, substituted or unsubstituted $C_{5-10}$ heteroaryl; where $R^3$ and $R^4$ are each independently selected from the group consisting of substituted or unsubstituted $C_{1-8}$ alkyl, substituted or unsubstituted $C_{3-6}$ cycloalkyl, $C_{1-10}$ alkoxy, $C_{1-12}$ alkylamino, substituted or unsubstituted $C_{3-10}$ heterocyclyl, substituted or unsubstituted $C_{6-10}$ aryl, substituted or unsubstituted $C_{5-10}$ heteroaryl and substituted or unsubstituted arylalkyl; where $R^3$ and $R^4$ together with the atoms to which they are attached may form a ring; and where $M^1$ and $M^2$ are each a counterion independently selected from the group consisting of Group I metal ions and Group II metal ions; the improvement comprising generating the chiral catalyst in situ.

Further, there is disclosed a catalyst for stereoselective reactions prepared by the step of combining an alkenyl ligand and a deprotonated chiral ligand in the presence of a ruthenium (II) metal; wherein the alkenyl ligand is of formula (I):

(I)

where $R^5$ is selected from the group consisting of hydrogen, $C_{1-8}$ alkyl, $C_{6-10}$ aryl, $C_{5-10}$ heteroaryl, $C_{3-10}$ heterocycle; and where $R^6$ is selected from the group consisting of hydrogen, and $C_{1-8}$ alkyl; and where $R^5$ and $R^6$ together with the atoms to which they are attached may form a carbocyclic ring; wherein the deprotonated chiral ligand is of formula (III):

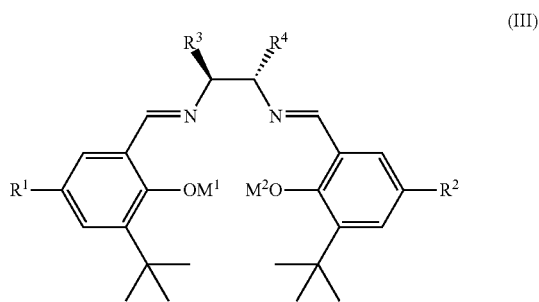

(III)

where $R^1$ and $R^2$ are each independently selected from the group consisting of hydrogen, substituted or unsubstituted $C_{1-8}$ alkyl, substituted or unsubstituted $C_{6-10}$ aryl, substituted or unsubstituted $C_{3-10}$ heterocyclyl, substituted or unsubstituted $C_{5-10}$ heteroaryl; where $R^3$ and $R^4$ are each independently selected from the group consisting of substituted or unsubstituted $C_{1-8}$ alkyl, substituted or unsubstituted $C_{3-8}$ cycloalkyl, $C_{1-10}$ alkoxy, $C_{1-12}$ alkylamino, substituted or unsubstituted $C_{3-10}$ heterocyclyl, substituted or unsubstituted $C_{6-10}$ aryl, substituted or unsubstituted $C_{5-10}$ heteroaryl and substituted or unsubstituted arylalkyl; where $R^3$ and $R^4$ together with the atoms to which they are attached may form a ring; and where $M^1$ and $M^2$ are each a counterion independently selected from the group consisting of Group I metal ions and Group II metal ions.

DETAILED DESCRIPTION

Definitions

"Alkyl" by itself or as part of another substituent refers to a saturated hydrocarbon group which may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl include haloalkyl, perhaloalkyls, thioalkyl, aminoalkyl, and the like.

"Alkoxy" refers to —O-alkyl. Examples of an alkoxy group include methoxy, ethoxy, n-propoxy etc.

"Alkylamino" refers to —NHR' and —NR'R" where R' is alkyl and R is hydrogen or alkyl. Examples of alkylamino groups include methylamine, ethylamine, isopropylamine, butylamine, dimethyl amine, diisopropylamine and the like.

"Alkenyl" refers to an unsaturated hydrocarbon group which may be linear, cyclic or branched or a combination thereof. Alkenyl groups with 2-8 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups can be substituted or unsubstituted, unless otherwise indicated.

"Aryl" refers to a polyunsaturated, aromatic hydrocarbon group having a single ring (monocyclic) or multiple rings (bicyclic), which can be fused together or linked covalently. Aryl groups with 6-10 carbon atoms are preferred, where this number of carbon atoms can be designated by $C_{6-10}$, for example. Examples of aryl groups include phenyl and naphthalene-1-yl, naphthalene-2-yl, biphenyl and the like. Aryl groups can be substituted or unsubstituted, unless otherwise indicated.

"Heterocyclyl" refers to a saturated or unsaturated non-aromatic ring containing at least one heteroatom (typically 1 to 5 heteroatoms) selected from nitrogen, oxygen, sulfur or silicon. The heterocyclyl ring may be monocyclic or bicyclic. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like.

"Heteroaryl" refers to an aromatic group containing at least one heteroatom, where the heteroaryl group may be monocyclic or bicyclic. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl.

Heterocyclyl and heteroaryl can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Heterocyclyl and heteroaryl groups can be substituted or unsubstituted, unless otherwise indicated. For substituted groups, the substitution may be on a carbon or heteroatom.

Suitable substituents for substituted alkyl, substituted alkenyl, and substituted alkynyl include halogen, —CN, —$CO_2R'$, —C(O)R, —C(O)NR'R", oxo (=O or —O⁻), —OR', —OC(O)R', —OC(O)NR'R"—NO₂, —NR'C(O)R', —NR'''C(O)NR'R'', —NR'R'', —NR'CO₂R'', —NR'S(O)R', —NR'S(O)₂R''', —NR'''S(O)NR'R'', —NR'''S(O)₂NR'R'', —SR', —S(O)R', —S(O)₂R', —S(O)₂NR'R'', —NR'—C(NHR'')=NR''', —SiR'R''R''', —N₃, substituted or unsubstituted $C_{6-10}$ aryl, substituted or unsubstituted 5- to 10-membered heteroaryl, and substituted or unsubstituted 3- to 10-membered heterocyclyl. The number of possible substituents range from zero to (2m'+1), where m' is the total number of carbon atoms in such radical.

Suitable substituents for substituted aryl, substituted heteroaryl and substituted heterocyclyl include halogen, —CN, —CO₂R', —C(O)R', —C(O)NR'R'', oxo (=O or —O⁻), —OR', —OC(O)R', —OC(O)NR'R'', —NO₂, —NR'C(O)R'', —NR'''C(O)NR'R'', —NR'R'', —NR'CO₂R'', —NR'S(O)R'', —NR'S(O)₂R'', —NR'''S(O)NR'R'', —NR'''S(O)₂NR'R'', —SR', —S(O)R', —S(O)₂R', —S(O)₂NR'R'', —NR'—C(NHR'')=NR''', —SIR'R''R''', —N₃, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10 membered heterocyclyl. The number of possible substituents range from zero to the total number of open valences on the aromatic ring system.

As used above, R', R and R'' each independently refer to a variety of groups including hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, substituted or unsubstituted arylalkyl, substituted or unsubstituted aryloxyalkyl. When R' and R'' are attached to the same nitrogen atom, they can be combined with the nitrogen atom to form a 3-, 4-, 5-, 6-, or 7-membered ring (for example, —NR'R'' includes 1-pyrrolidinyl and 4-morpholinyl). Furthermore, R' and R'', R and R', or R' and R''' may together with the atom(s) to which they are attached, form a substituted or unsubstituted 5-, 6- or 7-membered ring.

"Heteroatom" is meant to include oxygen (O), nitrogen (N), sulfur (S) and silicon (Si).

It will be apparent to one skilled in the art that certain compounds of the present invention may exist in tautomeric forms, all such tautomeric forms of the compounds being within the scope of the invention. Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-11 ($^{14}$C). All isotopic variations of the compounds of the present invention, whether radioactive or not, are intended to be encompassed within the scope of the present invention.

The term "asymmetric" refers to a molecule lacking all traditional elements of symmetry.

The term "carbocyclic ring" refers to a 5-10 membered ring in which the all of the ring atoms are carbons. A carbocyclic ring may be aromatic or nonaromatic.

The term catalysis or "catalyzed" refers to a process in which a relatively small amount of a material increases the rate of a chemical reaction and is not itself consumed in the reaction.

The term "catalytic amount" refers to a substoichiometric amount of the catalyst relative to a reactant.

The term "chiral" refers to a molecule or conformation which is not superimposable with its mirror image partner.

"Chiral catalyst" refers to a molecule which is not superimposable with its mirror image partner and that increases the rate of a chemical reaction without itself being consumed. In a stereoselective catalytic reaction, the chiral catalyst will serve to catalyze the reaction, while also providing enantioselectivity.

"Chiral ligand" refers to a molecule or ion that surrounds a metal, especially a transition metal, in a metal ion complex as a Lewis base, where the molecule in one which is not superimposable with its mirror image partner.

"Complex" refers to a coordination compound formed by the union of one or more electronically rich molecules or atoms capable of independent existence with one or more electronically poor molecules or atoms, which is also capable of independent existence.

"Diastereomer" refers to one of a group of stereoisomers which is not related to another stereoisomer of the group as a mirror image.

"Diastereoselective" refers to a process which favors production of one of the two possible diastereomers of a reaction product. For example, a chemical reaction would be diastereoselective if it produces the two diastereomers of a chiral product in unequal amounts. Such a reaction is said to exhibit diastereoselectivity.

"Enantiomer" refers to one of a pair of molecular species that are mirror images of each other and not superimposable.

"Enantiomerically enriched" refers to a mixture of enantiomers, in which one of the enantiomers is present in a greater amount than the partner enantiomer. An "enantiomerically enriched" product will have an enantiomeric excess ("% ee"), of more than 0 but less than 100%. "Enantiomeric excess" (ee) is equal to 100 times the mole fraction of the major enantiomer minus the mole fraction of the minor enantiomer. In a mixture of a pure enantiomer (R or S) and a racemate, ee is the percent excess of the enantiomer over the racemate. Representative of an enantiomerically enriched sample is a mixture of 25% of one enantiomer and 75% of the partner enantiomer. The mole fractions of each enantiomer are 0.25 and 0.75 respectively. The enantiomeric excess is calculated as (0.75−0.25)×100=50. Thus, the enantiomerically enriched sample has an ee of 50%.

"Enantioselective" refers to a process which favors production of one of the two possible enantiomers of a reaction product. For example, a chemical reaction would be enantioselective if it produces the two enantiomers of a chiral product in unequal amounts. Such a reaction is said to exhibit enantioselectivity.

"Ligand" refers to a molecule or ion that surrounds a metal, especially a transition metal, in a complex and serves as a Lewis base (i.e. an electron pair donor).

"Metal" refers to elements located in Groups 5 and 6 of the periodic table with atomic numbers of 23 to 74.

"Phosphorus donating ligand" refers to a ligand containing a phosphorus atom, where the phosphorus atom can act as the Lewis base and electron pair donor to form a complex with a metal. Examples include triphenylphosphine, tributylphosphine and the like.

"Pyridyl donating ligand refers to a pyridine compound which can act as a ligand, where the nitrogen atom of the pyridine ring can act as the Lewis base and electron pair donor to form a complex with a metal. A pyridyl donor ligand can be substituted or unsubstituted.

"Stereoisomer" refers to isomers of identical constitution (i.e. bond connectivity), but which differ in their arrangement in space.

"Stereoselective" refers to preferentially forming one stereoisomer over another in a chemical reaction. If the stereoisomers are enantiomers, the chemical reaction is an enantioselective reaction. If the stereoisomers are diastereomers, the chemical reaction is a diastereoselective reaction.

"Tertiary amine ligand" refers to nitrogen atom which is substituted with three groups other than hydrogen. Suitable substituents include alkyl and aryl groups. The tertiary amine ligand contains a nitrogen atom that can act as a Lewis base and electron pair donor to form a complex with a metal.

The term "carbene precursor" refers to a compound used to generate a carbene at the coordination site of a transition metal.

Chiral Catalyst

In a first aspect of the first embodiment, a chiral catalyst is formed by combining a deprotonated chiral ligand, an alkenyl ligand and a ruthenium (II) metal. A ruthenium (II) metal is any ruthenium metal with an oxidation state of 2 Examples of ruthenium (II) metals include ruthenium (I) chloride ($RuCl_2$); ruthenium (II) bromide ($RuBr_2$); ruthenium (II) iodide ($RuI_2$); tricarbonyldichlorodiruthenium(II) dimmer ($[RuCl_2(CO)_3]_2$); $K_4[Ru(CN)_6] \cdot 3H_2O$; bis(cyclopentadienyl)ruthenium (II) ($Ru(C_5H_5)_2$); bis(pentamethylcyclopentadienyl)ruthenium (II) ($Ru(C_5Me_5)_2$); dichloro($\eta^4$-cyloocta 1,5-diene)ruthenium(II); dichloro(1,5-cyclooctadiene)ruthenium(II); tetrachlorobis(4-cymene)diruthenium(II), and tetrachlorobis ($\eta^6$-p-cymene)diruthenium(II) ($[RuCl_2(p\text{-cymene})]_2$). Preferably the ruthenium (II) metal is $[RuCl_2(p\text{-cymene})]_2$.

Alkenyl Ligand

In one aspect of the first embodiment of the present invention an alkenyl ligand is provided of the formula (I):

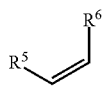

(I)

where $R^5$ is selected from the group consisting of hydrogen, substituted or unsubstituted $C_{1-8}$ alkyl, substituted or unsubstituted $C_{6-10}$ aryl, substituted or unsubstituted $C_{5-10}$ heteroaryl, and substituted or unsubstituted $C_{3-10}$ heterocycle; and $R^6$ is selected from the group consisting of hydrogen and substituted or unsubstituted $C_{1-8}$ alkyl; or $R^5$ and $R^6$ together with the atoms to which they are attached may form a carbocyclic ring.

In one embodiment, the alkenyl ligand is of formula II:

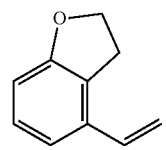

(II)

which is also referred to as 2,3-dihydro-4-vinylbenzofuran.

In another embodiment, the alkenyl ligand is selected from the group consisting of ethylene, cyclohexene, 1-hexene and 2,3-dihydro-4-vinylbenzofuran.

In one embodiment, $R^5$ is selected from the group consisting of hydrogen, substituted or unsubstituted $C_{1-8}$ alkyl, and substituted or unsubstituted $C_{3-10}$ heterocycle.

In one embodiment, $R^6$ is hydrogen.

In one embodiment, $R^6$ is hydrogen, and $R^5$ is other than hydrogen.

In another embodiment, $R^6$ is hydrogen, and $R^5$ is substituted or unsubstituted $C_{3-10}$ heterocycle.

In another embodiment $R^6$ is hydrogen, and $R^5$ is substituted or unsubstituted $C_{1-8}$ alkyl.

In another embodiment, $R^6$ and $R^5$ are each independently substituted or unsubstituted $C_{1-8}$ alkyl.

Deprotonated Chiral Ligand

The deprotonated chiral ligand of the present invention is of the formula (III)

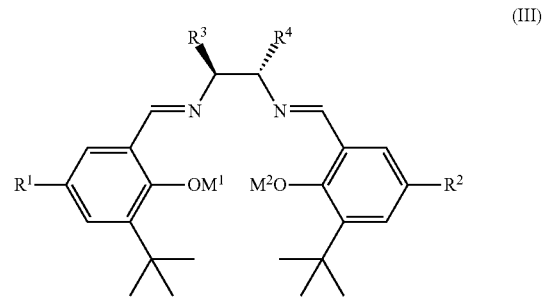

(III)

where $R^1$ and $R^2$ are each independently selected from the group consisting of hydrogen, substituted or unsubstituted $C_{1-8}$ alkyl, substituted or unsubstituted $C_{1-10}$ aryl, substituted or unsubstituted $C_{3-10}$ heterocyclyl, and substituted or unsubstituted $C_{5-10}$ heteroaryl;

$R^3$ and $R^4$ are each independently selected from the group consisting of substituted or unsubstituted $C_{1-8}$ alkyl, substituted or unsubstituted $C_{3-8}$ cycloalkyl, $C_{1-10}$ alkoxy, $C_{1-12}$ alkylamino, substituted or unsubstituted $C_{3-10}$ heterocyclyl, substituted or unsubstituted $C_{6-10}$ aryl, substituted or unsubstituted $C_{5-10}$ heteroaryl, and substituted or unsubstituted arylalkyl; or $R^3$ and $R^4$ together with the atoms to which they are attached may form a ring;

$M^1$ and $M^2$ are each a counterion. Preferably, $M^1$ and $M^2$ are the same but they may be different. More preferably, $M^1$ and $M^2$ are each independently selected from Group I or Group II metal ions. Group I metals are Li, Na, K, Rb, Cs and Fr. Group II metals are Be, Mg, Ca, Sr, Ba, and Ra. Even more preferably, $M^1$ and $M^2$ are selected from the group consisting of $Li^+$, $Na^+$, $MgCl^+$ and $MgBr^+$. Most preferably, $M^1$ and $M^2$ are each $Li^+$.

In one embodiment, the deprotonated chiral ligand is of the formula (IV):

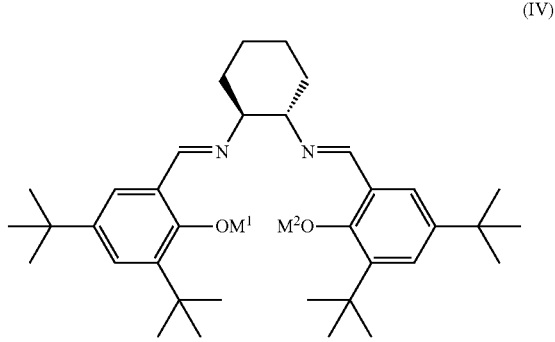

(IV)

also referred to as 1,2-cyclohexanediamino-N,N'-bis(3,5-di-t-butyl-salicylidene). Preferably, the chiral ligand is the (1R,2R)-(−) enantiomer. In other embodiments, the (1S,2S)-(+) enantiomer is preferred.

In one embodiment, $R^1$ and $R^2$ are each independently selected from the group consisting of substituted or unsubstituted $C_{1-8}$ alkyl, and substituted or unsubstituted $C_{6-10}$ aryl.

In another embodiment, $R^1$ and $R^2$ are each independently substituted or unsubstituted $C_{1-8}$ alkyl.

In another embodiment, $R^1$ and $R^2$ are each independently a perfluoro $C_{1-8}$ alkyl.

In a highly preferred embodiment, $R^1$ and $R^2$ are each t-butyl.

In one embodiment, $R^3$ and $R^4$ are each independently selected from the group consisting of substituted or unsubstituted $C_{1-8}$ alkyl, and substituted or unsubstituted $C_{6-10}$ aryl.

In another embodiment, $R^3$ and $R^4$ are each independently a substituted or unsubstituted $C_{1-8}$ alkyl.

In a highly preferred embodiment, $R^3$ and $R^4$ together with the atoms to which they are attached form a cyclohexane ring.

Method of Forming the Chiral Catalyst

In an illustrative embodiment, the chiral catalyst was prepared by combining the ruthenium (II) metal, the deprotonated chiral ligand and alkenyl ligand. The deprotonated chiral ligand, formula (III) where $M^1$ and $M^2$ are metal ions from Group I or Group II, may be formed by deprotonating the phenolic groups of the chiral ligand with a suitable base as shown in Scheme 1.

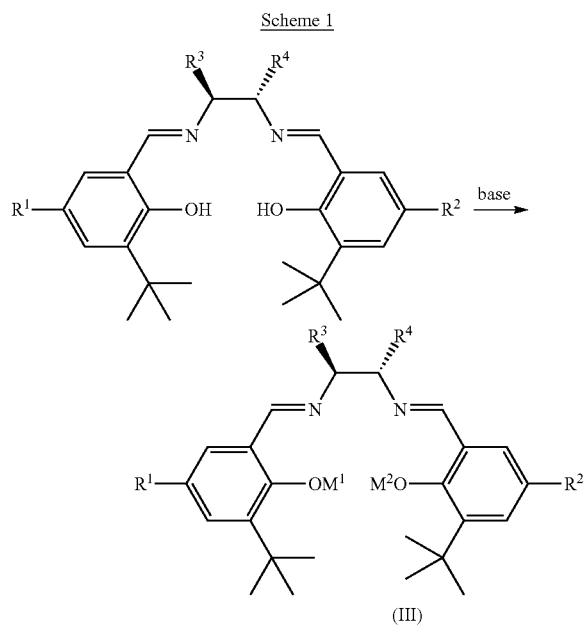

To promote complexation of the chiral ligand with the ruthenium (II) metal, the chiral ligand was deprotonated with a base, with deprotonation occurring at both hydroxyl groups to form phenoxide anions. Any suitable base known to one skilled in the art to deprotonate a phenol may be employed to deprotonate the chiral ligand. Suitable bases include metal amines, including for example, lithium diisopropylamine $(LiN(CH(CH_3))_2$; metal alkoxides including for example potassium tert-butoxide, sodium ethoxide, sodium methoxide; and metal alkyls, including for example methyl lithium, n-butyl lithium, t-butyl lithium, hexyl lithium, octyl lithium, methylmagnesium bromide, methylmagnesium chloride and the like. Preferably the base is lithium diisopropylamide $(LiN(CH(CH_3)_2)_2)$. Preferably at least two mole equivalents of base are used as compared to the chiral ligand.

The deprotonation of the chiral ligand may be performed in any suitable inert solvent known to one skilled in the art. Preferably the solvent is tetrahydrofuran (THF). The deprotonation is conducted at a suitable temperature to deprotonate the phenol groups of the chiral ligand. Preferably the deprotonation is conducted at about less than 15° C., more preferably less than about 10° C., even more preferably between about 0 and about 10° C.

The deprotonated phenoxide groups of the chiral ligand coordinate with the ruthenium (II) metal to form a complex. Due to the chirality of the chiral ligand, complexation of the deprotonated chiral ligand with the ruthenium (II) metal imparts chirality to the ruthenium catalyst. The chiral nature of the catalyst influences the stereoselectivity of the cyclopropanation reaction.

An alkenyl ligand was also combined with ruthenium (II) metal and the deprotonated chiral ligand. Without wishing to be bound by theory, the alkenyl ligand is believed to coordinate to the ruthenium (II) metal and occupy an axial coordination site, forming a catalyst of formula (V) or (VI), depending upon whether one or two alkenyl ligands coordinate.

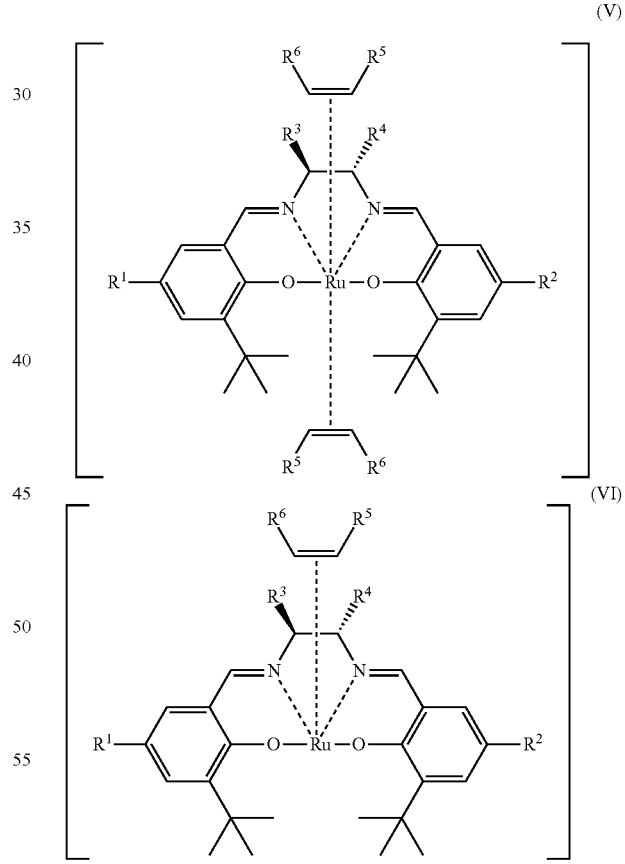

Strong donor ligands such as pyridyl donating ligands, phosphorus donating ligands and tertiary amine ligands have been used previously with ruthenium (II) catalysts and are thought to occupy an axial coordination position on the ruthenium (II) metal. Pyridyl donating ligands are pyridine compounds which can act as a ligand, where the nitrogen atom of the pyridine ring acts as the Lewis base and electron pair donor to form a complex with the ruthenium metal. A phosphorus donating ligand is a ligand containing a phosphorus atom, where the phosphorus atom can act as the Lewis base and electron pair donor to form a complex with the ruthenium metal. A tertiary amine ligand is where the nitrogen atom acts as a Lewis base and electron pair donor to form a complex with the ruthenium metal.

Without wishing to be bound by theory, the present invention provides alkenyl ligands which are thought to occupy an axial coordination position on the ruthenium (II) metal. Pyridyl donating ligands, phosphorus donating ligands and tertiary amine ligands are preferably not employed in the catalyst preparation or cyclopropanation reaction. Better stereoselectivity such as enantioselectivity and higher yields have been found in the present invention when alkenyl ligands are used as compared to pyridyl or phosphorus donating ligands.

The combination of the alkenyl ligand, ruthenium (II) metal and deprotonated chiral ligand forms a catalyst which is active. Although in some cases it may be desirable to isolate the catalyst, preferably the catalyst is formed in situ, not isolated, and not purified prior to use in the cyclopropanation reaction. Generating the catalyst in situ offers advantages over using a isolated catalyst such as: (i) convenience; and (ii) minimal handling of a catalyst which may be air or moisture sensitive. Without wishing to be bound by theory, the properties which make a catalyst stable enough for isolation, may also decrease the reactivity of the catalyst. Using an in situ catalyst may allow a more reactive catalyst to be used that gives better selectivity, yield and turnover than using an isolated catalyst.

In one embodiment, the formula of the alkenyl ligand is the same as the formula of the alkenyl substrate to be used in the cyclopropanation reaction. This minimizes the generation of impurities. For example, when the alkenyl ligand is different than the alkenyl substrate, the alkenyl ligand can enter into transition metal catalyzed side reactions known to one skilled in the art, and form impurities. When the alkenyl ligand is the same as the alkenyl substrate, impurities are minimized.

The combining of the ruthenium (II) metal, alkenyl ligand, and deprotonated chiral ligand may be done in any suitable order. In some aspects it may be desirable to generate the deprotonated chiral ligand in the presence of the ruthenium (II) metal and or alkenyl ligand, for example, when ruthenium (II) metal and the functional groups on the alkenyl ligand are compatible with the deprotonation conditions. The deprotonated chiral ligand is formed by deprotonating the phenol groups of the chiral ligand with a suitable base as discussed previously.

The catalyst preparation reaction is carried out with various amounts of metal, deprotonated chiral ligand and alkenyl ligand. The amount of deprotonated chiral ligand used can be greater than the amount of ruthenium (II) metal. Preferably at least one equivalent of the deprotonated chiral ligand relative to the ruthenium (II) metal is used. The amount of alkenyl ligand is at least twice the amount of the ruthenium (II) metal, preferably at least 5 equivalents, more preferably at least 6 equivalent of the alkenyl ligand relative to the ruthenium (II) metal. In aspects where the alkenyl ligand is the same as the alkenyl substrate, a large excess of alkenyl ligand may be employed relative to the ruthenium (II) metal.

The combining of the ruthenium (II) metal, deprotonated chiral ligand and alkenyl ligand is preferably done in a suitable solvent, for a suitable length of time, and at a suitable temperature. Suitable solvents include tetrahydrofuran (THF), and combinations of THF/cyclohexane. The ruthenium (II) metal, deprotonated chiral ligand and alkenyl ligand are combined at a suitable temperature. A suitable temperature for combining the ruthenium (II) metal, deprotonated chiral ligand and alkenyl ligand is between about −10° C. and about 30° C., preferably between about 0° C. and about 25° C., more preferably between about 0° C. and about 5° C. After combining the ruthenium (II) metal, deprotonated chiral ligand and alkenyl ligand, the mixture is stirred for a suitable amount of time to allow the catalyst to form. The mixture is stirred for at least 12 h, preferably at least 1 h, more preferably at least 5 minutes.

Method of Stereoselective Cyclopropanation

In one embodiment of the present invention, a method of stereoselective cyclopropanation is provided. In the cyclopropanation method, the catalyst is contacted with a carbene precursor in the presence of an alkenyl substrate.

Carbene Precursor

A carbene precursor is a compound used to generate a carbene at the coordination site of a transition metal, in particular at the coordination site of ruthenium. Preferably, the carbene precursor is a diazo compound wherein the carbene is generated by the removal of $N_2$ as nitrogen gas from the solution. Examples of diazo compounds which are carbene precursors include ethyl diazoacetate, t-butyl diazoacetate, 2,3,4-trimethyl-3-pentyl diazoacetate, menthyl diazoacetate, 2,5-dimethyl-4-hexen-2-yl diazoacetate, 3-(diazoacetyl) amino propionate, and diazoacetylamino acetate.

In one embodiment, the carbene precursor is a diazoester.

In one embodiment, the carbene precursor is selected from the group consisting of ethyl diazoacetate, t-butyl diazoacetate, and menthyl diazoacetate.

In another embodiment, the carbene precursor is ethyl diazoacetate.

In one embodiment, the carbene precursor is of the formula (VII):

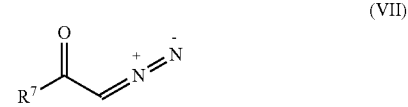

(VII)

where $R^7$ is selected from the group consisting of substituted or unsubstituted $C_{1-8}$ alkyl, substituted or unsubstituted $C_{3-8}$ cycloalkyl, $C_{1-10}$ alkoxy, $C_{1-12}$ alkylamino, substituted or unsubstituted $C_{3-10}$ heterocyclyl, substituted or unsubstituted $C_{6-10}$ aryl, substituted or unsubstituted $C_{6-10}$ heteroaryl and substituted or unsubstituted arylakyl.

In one embodiment, $R^7$ is selected from the group consisting of substituted or unsubstituted $C_{1-8}$ alkyl, $C_{1-10}$ alkoxy, $C_{1-12}$ alkylamino, and substituted or unsubstituted $C_{6-10}$ aryl.

In another embodiment, $R^7$ is selected from the group consisting of substituted or unsubstituted $C_{1-8}$ alkyl, and $C_{1-10}$ alkoxy.

In one preferred embodiment, $R^7$ is $C_{1-10}$ alkoxy.

In another preferred embodiment, $R^7$ is selected from the group consisting of —OEt, -OtBu, and —O-(menthyl).

Alkenyl Substrate

In the stereoselective cyclopropanation method, the catalyst is contacted with the carbene precursor in the presence of an alkenyl substrate. The carbon atoms of the alkenyl substrate form two of the carbon atoms of the cyclopropyl ring that is formed. Any suitable alkenyl substrate can be used which leads a cyclopropyl product which is enriched in one stereoisomer. Preferably the alkenyl substrate is a terminal alkene of formula (VIII):

(VIII)

where $R^8$ is selected from the group consisting of halogen, —CN, —C(O)$R^a$, —CO$_2$$R^a$, —C(O)NR$^a$$R^b$, —O$R^a$, —OC(O)$R^a$, —OC(O)NR$^a$$R^b$, —S$R^a$, —S(O)$R^a$, —S(O)$_2$$R^a$, —S(O)$_2$NR$^a$$R^b$, —NO$_2$, —NR$^a$$R^b$, —NR$^a$C(O)$R^b$, —NR$^a$C(O)O$R^b$, —NR$^a$S(O)$_2$$R^b$, —NR$^a$C(O)NR$^b$$R^c$, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl;

where $R^a$, $R^b$, and $R^c$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl; $R^a$ and $R^b$, $R^b$ and $R^c$ or $R^a$ and $R^c$ may, together with the atoms to which they are attached, form a substituted or unsubstituted 5-, 6-, or 7-membered ring; and where $R^9$ is selected from the group consisting of hydrogen, and $C_{1-6}$ alkyl.

In one embodiment, the alkenyl substrate is of formula (II):

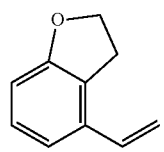

(II)

which is also referred to as 2,3-dihydro-4-vinylbenzofuran and VBF, herein.

In one embodiment, $R^8$ is selected from the group consisting of halogen, —CN, —C(O)$R^a$, —CO$_2$$R^a$, —C(O)NR$^a$$R^b$, —S(O)$R^a$, —S(O)$_2$$R^a$, —S(O)$_2$NR$^a$$R^b$, and —NO$_2$.

In another embodiment, $R^8$ is selected from the group consisting of —O$R^a$, —S$R^a$, and —NR$^a$$R^b$.

In another embodiment, $R^8$ is selected from the group consisting of substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl.

In another embodiment, $R^8$ is selected from the group consisting of substituted or unsubstituted 3- to 10-membered heterocyclyl, substituted or unsubstituted $C_{6-10}$ aryl, and substituted or unsubstituted 5- to 10-membered heteroaryl.

In another embodiment, $R^8$ is substituted or unsubstituted 3- to 10-membered heterocyclyl.

In one embodiment, $R^9$ is hydrogen.
In another embodiment, $R^9$ is $C_{1-8}$ alkyl.
In another embodiment, $R^9$ is methyl.

Cyclopropyl Product

In the stereoselective cyclopropanation method, a cyclopropyl product is formed which is enriched in one stereoisomer. Preferably the cyclopropatiion method is enantioselective wherein one enantiomer is formed preferentially as compared to the partner enantiomer. As an illustrative example, when the carbene precursor is of formula (VII) and the alkenyl substrate is of formula (VIII), a cyclopropyl product of formula (IX) is formed according to the following scheme:

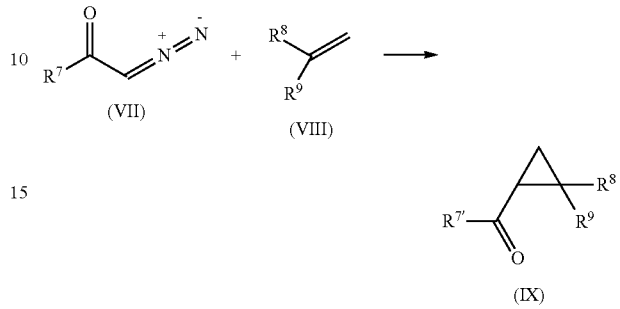

where $R^7$, $R^8$, and $R^9$ are as defined above. The cyclopropyl product is formed in at least 50% yield, preferably at least 80%, more preferably at least 90% and even more preferably at least 95%.

The cyclopropyl product has a cis or trans configuration, depending on the relative size and nature of $R^8$ and $R^9$. When $R^9$ is hydrogen, preferably the trans product is formed as shown in the following scheme.

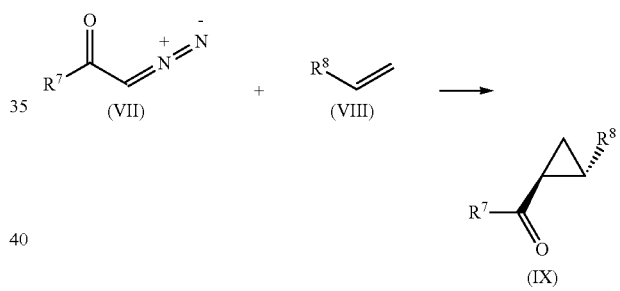

The amount of trans cyclopropyl product formed in comparison to cis cyclopropyl product is determined by dividing the amount of trans cyclopropyl product by the sum of the amount of cis and trans cyclopropyl products, and multiplying this number by 100. The amount of cis or trans product can be measured in either moles or mass. Preferably the trans cyclopropyl product is formed in greater than about 80%, more preferably greater than about 90% and even more preferably greater than about 95%.

Each of the cis and trans isomers can be evaluated for enantiomeric excess. Enantiomeric excess (ee) is equal to 100 times the mole fraction of the major enantiomer minus the mole fraction of the minor enantiomer. The enantiomeric excess is preferably greater than about 80%, more preferably greater than about 90%.

The stereoselective cyclopropanation reaction is carried out with various amounts of catalyst, carbene precursor and alkenyl substrate. The amount of carbene precursor and alkenyl substrate may be the same or one may be used in excess. In this case, the reagent present in the lesser amount is referred to as the limiting reagent. Preferably the alkenyl substrate is the limiting reagent.

An advantage of the present invention is that the cyclopropanation reaction can be carried out with good stereoselectivity and in high yield when the alkenyl substrate is used as the limiting reagent. This is particularly important when the alkenyl substrate requires a laborious synthesis or is costly to synthesize or purchase.

Another advantage of the present invention is that the cyclopropanation reaction can be carried out with good stereoselectivity and in high yield without using a large excess of the carbene precursor. Often a reaction is driven to completion by using a large excess of the non-limiting reagent, for example 5-fold, 10-fold or even greater excess of the non-limiting reagent. When the non-limiting reagent is the carbene precursor, such as a diazo compound, use of an excess of the diazo compound creates an unsafe operating condition, especially on large scale such as in a manufacturing plant. The use of excess diazo compound such as diazoesters is undesirable due to: (i) the build-up of the diazo compound in the reactor; diazo compounds can be explosive and the reactor concentration of this reagent must be kept low; (ii) the rapid addition of the diazo compound can lead to an exothermic reaction that can be difficult to control; (iii) for each mole of the diazo compound that is consumed, a mole of nitrogen is released; a rapid increase in the rate of the reaction in the presence of a high concentration of the diazo compound could release a bulbous amount of nitrogen that may not be able to be effectively vented from the reactor, thus leading to a pressure build-up in the reactor and creating an unsafe condition; (iv) the use of a large excess of diazo compound creates an unsafe condition, requires the handling, transporting and storage of excess diazo compound than theoretically required in the reaction which is significant at manufacturing scale, requires extra monitoring to determine the fate of the excess diazo compound used in the reaction, and is inefficient.

Accordingly, preferably the alkenyl substrate is used as the limiting reagent and less than about 2.0 equivalents of the carbene precursor is used in the stereoselective cyclopropanation reaction. In another embodiment, when the alkenyl substrate is the limiting reagent, between about 1.05 and about 2.0 equivalents of the carbene precursor are used as compared to the limiting reagent, preferably between about 1.1 and about 1.8, more preferably between about 1.2 and about 1.5 equivalents, even more preferably about 1.3 equivalents.

The metal catalyst is used in amount of at least 0.05 mole % of the limiting reagent, preferably between about 0.05% to about 10%, more preferably between about 0.1 to about 5%, even more preferably between about 0.5% and 3%.

The stereoselective cyclopropanation reaction is carried out in a solvent, with organic solvents being preferred. Preferably reaction solvent is THF or toluene, or a combination thereof. Additional solvents such as cyclohexane may also be present. A single solvent may be used, or a combination of solvents may be used.

The stereoselective cyclopropanation reaction is preferably carried out at a suitable reaction temperature. Any suitable temperature may be chosen which affords the desired yield and stereoselectivity of the cyclopropyl product. The reaction temperature is usually below or at the boiling point of the solvent. Preferably the reaction temperature is between about 0° C. and about 40° C., more preferably between about 20° C. and about 30° C.

The stereoselective cyclopropanation reaction is carried out for a suitable time to afford the desired yield and stereoselectivity of the cyclopropyl product. Alternatively, the reaction can be carried out for a suitable time to consume the limiting reagent. The reaction time is at least 1 h, preferably between about 1 h and about 10 h, more preferably between abut 2 h and about 5 h.

It is important to note that one skilled in the art would realize that optimization of the yield and the stereoselectivity can be achieved by altering the reaction conditions. For example, such optimization can include changing the solvent, the temperature of various stages of the reaction, the equivalents the metal catalyst, the equivalents of the carbene precursor, and the equivalents of the alkenyl substrate.

The following examples are offered to illustrate, but not to limit, the claimed invention.

EXAMPLES

Reagents and solvents used below can be obtained from commercial sources such as Aldrich Chemical Co. (Milwaukee, Wis., USA) unless otherwise indicated. The salen complex was obtained from Strem Chemicals, Inc. $^1$H-NMR were recorded on an NMR spectrometer. Significant peaks are tabulated in the order: multiplicity (br, broad; s, singlet; d, doublet; t, triplet; q, quartet; m, multiplet) and number of protons. Mass spectrometry results are reported as the ratio of mass over charge, followed by the relative abundance of each ion (in parenthesis). A single mle value is reported for the M+H (or, as noted, M−H, or M+Na) ion containing the most common atomic isotopes. Isotope patterns correspond to the expected formula in all cases.

Example 1

Rulsalenlcylcohexene Catalyst

In a 50-mL 3-neck neck round bottom flask fitted with a temperature probe, nitrogen inlet, magnetic stir bar and a septum was added (1R,2R)-(−)-1,2-cyclohexanediamino-N, N'-bis-(3,5-di-t-butylsalicyl idene) (salen; 2.17 g, 4 mmol) and 25 mL of anhydrous THF. The resultant solution was cooled to 0-5° C. Lithium diisopropylamide(tetrahydrofuran) (1.5 M solution in cyclohexane; 5.3 mL, 8 mmol) was added slowly at a rate that the reaction temperature was kept below 5° C. The solution was stirred for 1 hour at 0-5° C.

In a 250-mL round bottom flask was charged dichloro(p-cymene)ruthenium(II) dimer (1.21 g, 2 mmol), cyclohexene (0.92 g, 11.2 mmol) and anhydrous THF (60 mL). The mixture was stirred. The salen solution was added in one portion to the stirred suspension at ambient temperature. The salen reaction flask was rinsed with 10 mL of THF and the rinse solution was transferred to the 250-mL flask. The resultant mixture was stirred overnight. The catalyst solution can be used without further work-up in the cyclopropanation reaction as described below. Alternatively, the solution can be concentrated to dryness to provide a green solid that can be used in the cyclopropanation reaction.

Example 2

One Pot Procedure for Rulsalenlcylcohexene Catalyst

In a 50-mL round bottom flask fitted with a temperature probe, nitrogen inlet, magnetic stir bar and a septum was added (1R,2R)-(−)-1,2-cyclohexanediamino-N,N'-bis-(3,5-di-t-butylsalicylidene) (salen, 540 mg, 1 mmol) and 23.5 mL of anhydrous THF. The resulting solution was cooled to 0-5° C. To this was added LDA (1.5 M in cyclohexane, 1.34 mL, 2 mmol) at a rate that allowed the reaction temperature to be maintained below 5° C. The reaction mixture was stirred for 0.5 hour at 0-5° C. To this was added dichloro(p-cymene) ruthenium (II) dimer (300 mg, 0.5 mmol), followed by VBF (0.4 g, 2.8 mmol). After the addition, the mixture was stirred at ambient temperature. The catalyst solution can be used without further work-up in the cyclopropanation reaction as described below. Alternatively, the solution can be concentrated to dryness to provide a green solid that can be used in the cyclopropanation reaction.

Example 3

RulsalenII-Hexene Catalyst

The Ru/salen/1-hexene catalyst was prepared according to the procedure for Ru/salen/cyclohexene except that 1-hexene was used in place of cyclohexene. The resulting catalyst solution was found to be active in the cyclopropanation reaction of 4-vinyl-2,3-dihydrobenzofuran with ethyl diazoacetate.

Example 4

Rulsalenlethylene Catalyst

The Ru/salen/ethylene catalyst was prepared according to the procedure for Ru/salen/cyclohexene except that ethylene was used in place of cyclohexene. Excess ethylene gas was bubbled through a solution of dichloro(p-cymene)ruthenium (II) dimer in anhydrous THF, followed by addition of the deprotonated salen ligand. The resulting catalyst solution was found to be active in the cyclopropanation reaction of 4-vinyl-2,3-dihydrobenzofuran with ethyl diazoacetate.

Example 5

Representative Procedure for (1R,2R)-ethyl 2-(2,3-dihydrobenzofuran-4-yl)cyclopropanecarboxylate prepared using in situ generated rulsalenlethylene catalyst In a 3-neck neck round bottom flask fitted with a temperature probe, nitrogen inlet, magnetic stir bar and a septum was added (1R,2R)-(–)-1,2-cyclohexanediamino-N,N'-bis-(3,5-di-t-butylsalicylidene) (salen) and anhydrous THF. The resultant solution was cooled to 0-5° C. Lithium diisopropylamide(tetrahydrofuran) (1.5 M solution in cyclohexane; 2 equivalents) was added slowly at a rate that the reaction temperature was kept below 5° C. The solution was stirred for 1 hour at 0-5° C.

In a round bottom flask was charged dichloro(p-cymene) ruthenium(II) dimer (0.5 equivalents relative to the salen) and anhydrous THF and ethylene gas was bubbled through the solution. The mixture was stirred. The salen solution was added in one portion to the stirred suspension at ambient temperature. The salen reaction flask was rinsed with THF and the rinse solution was transferred to the round bottom flask. The resultant mixture was stirred overnight.

To a mixture of the in situ generated catalyst prepared in the previous paragraph was charged 4-vinyl-2,3-dihydrobenzofuran and toluene. To the stirred solution was added a solution of EDA in toluene. In some experiments, a second aliquot of EDA was charged. The solution was concentrated to remove the THF from the reaction solution. The remaining solution was transferred to a 3-neck round bottom flask equipped with a mechanical stirrer and temperature probe connected to a J-Kem controller. To the solution was added a solution of sodium hydroxide followed by tetra-n-butylammonium hydroxide. The mixture was stirred and heated to 60° C. The phases were separated and the organic phase was washed with water. The combined aqueous extracts were extracted with of toluene. The aqueous phase was combined with MTBE and cooled to 10° C. The pH of the aqueous phase was adjusted to 2-3 with phosphoric acid. The phases were mixed and then separated. The MTBE phase was washed with water. The MTBE phase was filtered through Whatman Qualitative #1 filter paper. The MTBE phase was concentrated to an oil

TABLE 1

Cyclopropanation of VBF with in situ Rulsalenlethyene catalyst

| Exp. | Reaction Temp. | Cis | Trans | VBF Remaining |
|---|---|---|---|---|
| 5 | 60° C.[a] | 4.3% | 83.8% | 11.8% |
| 6[b] | RT | 4.7% | 92.8% | 2.5% |
| 7 | 0-5° C. for 6 hours, then RT overnight.[c] | 6.4% | 94.6% | None Detected |
| 8[d] | RT | 5.1% | 94.9% | None Detected |
| 9[e] | RT | 4.8% | 92.6% | 2.6% |
| 10[f] | RT | 4.5% | 95.5% | None Detected |
| 11[g] | RT | 4.8% | 95.2% | None Detected |

[a]Started at RT and heated to 60° C.
[b]Slow addition of EDA. Mild exotherm observed.
[c]The reaction is slow at 0-5° C. and after warming to RT the reaction rate increases.
[d]Catalyst solution filtered through silica gel.
[e]Unfiltered catalyst solution used in Exp. 8.
[f]Used 1.2 eq of salen in catalyst synthesis.
[g]Same catalyst solution as used in exp. 10, except stored under $N_2$ at RT for 10 days prior to use.

The experiments in Table 1 used 2.6 equivalents of EDA relative to VBF, and 0.1-0.2 equivalents of catalyst. Experiments 5-6 illustrate that adding EDA at lower temperatures led to higher consumption of VBF. Experiments 9-10 illustrate that filtering the in situ catalyst solution led to higher consumption of VBF. Experiment 11 illustrates that freshly prepared in situ catalyst gives similar results to in situ catalyst that has been stored for 10 days.

Example 12

Ru/salen/4-vinyl-2,3-dihydrobenzofuran catalyst

The Ru/salen/4-vinyl-2,3-dihydrobenzofuran catalyst was prepared according to the procedure for Ru/salen/cyclohexene except that 4-vinyl-2,3-dihydrobenzofuran was used in place of cyclohexene. The resulting catalyst solution was found to be active in the cyclopropanation reaction of 4-vinyl-2,3-dihydrobenzofuran with ethyl diazoacetate.

Example 13

(1R,2R)-ethyl 2-(2,3-dihydrobenzofuran-4-yl)cyclopropanecarboxylate prepared using in situ Ru/salen/4-vinyl-2,3-dihydrobenzofuran catalyst

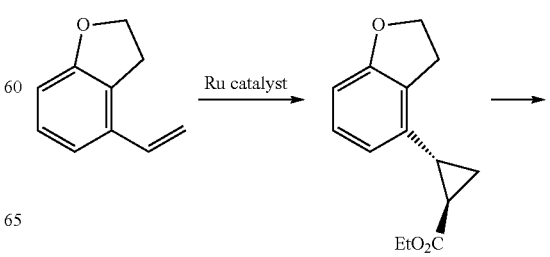

21
-continued

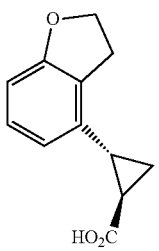

One mmol of the Ru/salen/4-vinyl-2,3-dihydrobenzofuran catalyst was prepared in situ in a total of 50 mL of anhydrous THF as described above in a 250 mL round bottom flask equipped with a mechanical stirrer, a temperature probe, a Claisen head fitted with a nitrogen inlet and an inlet for the addition of an ethyl diazoacetate (EDA) solution. To the in situ catalyst solution was charged 4-vinyl-2,3-dihydrobenzofuran (14.64 g, 100 mmol) in 15 mL of toluene. To the stirred solution was slowly added a solution of EDA (20.19 g, 180 mmol) in 90 mL of toluene via a Masterflex pump. A slight exotherm was noted but was easily controlled by the adjustment of the rate of EDA addition. After 3 hours, the VBF was consumed and 32 mL of the EDA solution was remaining. The remaining EDA solution was not added to the reaction vessel. Approximately 130 mmol of EDA or 1.3 equivalents were required to consume the VBF. The solution was concentrated to remove the THF from the reaction solution. Approximately 40 mL of solvent was removed. The remaining solution was transferred to a 500-mL 3-neck round bottom flask equipped with a mechanical stirrer and temperature probe connected to a J-Kem controller. To the solution was added a solution of sodium hydroxide (29.54 g 370 mmol, of 50% aqueous sodium hydroxide solution diluted with 120 mL of water) followed by tetra-n-butylammonium hydroxide (16.12 g, 33 mmol). The mixture was stirred and heated to 60° C. for 280 mins. The phases were separated and the organic phase was washed with 75 mL of water. The combined aqueous extracts were extracted with 75 mL of toluene. The aqueous phase was combined with 200 mL of MTBE and cooled to 10° C. The pH of the aqueous phase was adjusted to 2-3 with phosphoric acid. The phases were mixed and then separated. The MTBE phase was washed with 4×50 mL of water. The MTBE phase was filtered through Whatman Qualitative #1 filter paper. The MTBE phase was concentrated to an oil that solidified upon standing to give 22.13 g (95%) of a mixture of cyclopropyl acid isomers. 97.7:2.3 trans/cis by HPLC area counts; trans isomer (1R,2R) 91.8%:trans enantiomer (1S, 2S):8.2% by HPLC area counts; % enantiomeric purity (83.6% ee)

Example 14

Isolated Ru/salen/pyridine Catalyst

The isolated Ru/salen/pyridine catalyst was obtained from SonBinh Nguyen prepared according to the method of Miller et al (Angew. Chem Int. Ed. 2002, 41, 2953-2956). According to Miller et al. the Ru/salen/pyridine catalyst has the structure:

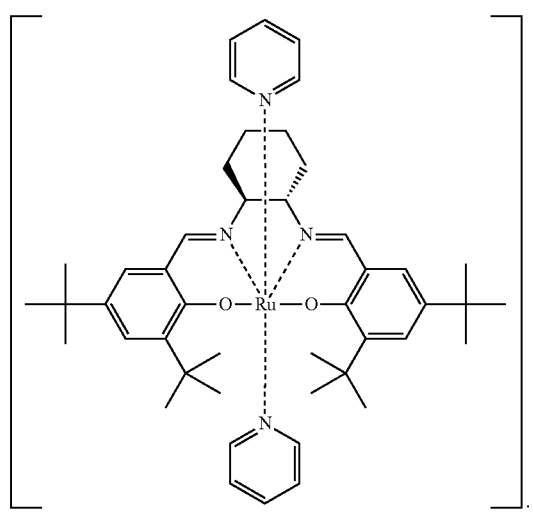

Example 15

(1R,2R)-ethyl 2-(2,3-dihydrobenzofuran-4-yl)cyclopropanecarboxylate prepared using isolated Ru/salen/pyridine catalyst To the isolated Ru/salen/pyridine (4 mg, 0.005 mmol) catalyst was charged 4-vinyl-2,3-dihydrobenzofuran (0.37 g, 2.53 mmol) in 4.44 mL of toluene. To the stirred solution was slowly added a solution of EDA (0.32 g, 2.80 mmol) in 1.0 mL of toluene over 30 minutes. After 2.5 hours, an aliquot was removed, and the sample was analyzed by in-process HPLC. The desired cyclopropane ethyl ester was not formed, and only VBF was detected. The catalyst was not active in the promotion of the cyclopropanation of VBF.

Example 16

Isolated Ru/salen/triphenylphosphine catalyst

The isolated Ru/salen/triphenylphosphine catalyst was obtained from SonBinh Nguyen prepared according to the method of Miller et al. (Angew. Chem Int. Ed. 2002, 41, 2953-2956). According to Miller et al. the Ru/salen/triphenylphosphine catalyst has the structure:

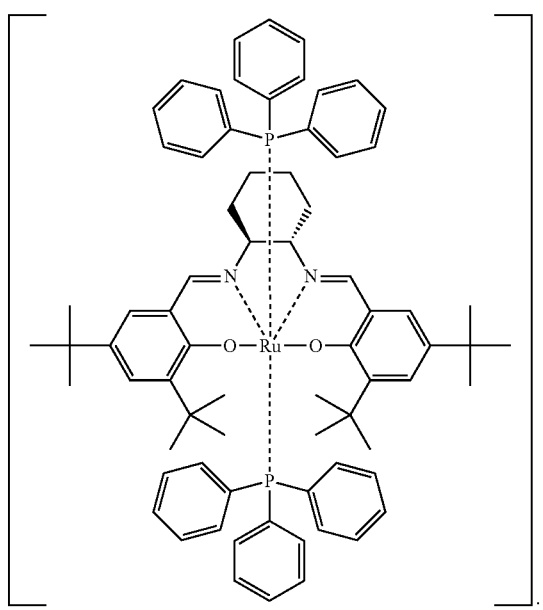

Experiment 17

(1R,2R)-ethyl 2-(2,3-dihydrobenzofuran-4-yl)cyclopropanecarboxylate prepared using isolated Ru/salen/triphenylphosphine catalyst To the isolated Ru/salen/triphenylphosphine (4 mg, 0.005 mmol) catalyst was charged 4-vinyl-2,3-dihydrobenzofuran (0.37 g, 2.53 mmol) in 4.4 mL of toluene. To the stirred solution was slowly added a solution of EDA (0.32 g, 2.80 mmol) in 1.0 mL of toluene over 15 minutes. After 2 hours, an aliquot was removed and analyzed by in-process HPLC. The cyclopropane ethyl ester was formed in just 4% (% AUC) yield, and after 20 hours the yield of the ethyl ester was unchanged.

Examples 15 and 17 illustrate the use of isolated Ru/salen/pyridine and Rulsalenltriphenylphosphinein the stereoselective cyclopropanation of 4-vinyl-2,3-dihydrobenzofuran. Neither of these isolated catalysts provided satisfactory results. Specifically, the reaction with the isolated Ru/salen/pyridine catalyst provided none of the desired (1R,2R)-ethyl 2-(2,3-dihydrobenzofuran-4-yl)cyclopropanecarboxylate product. The reaction with the isolated Rulsalenltriphenylphosphine catalyst provided only a small amount of the desired (1R,2R)-ethyl 2-(2,3-dihydrobenzofuran-4-yl)cyclopropanecarboxylate product. Without wishing to be bound by theory, the isolated Rulsalenlpyridine catalyst and isolated Rulsalenltriphenylphosphine catalyst may be unstable. The catalysts may degrade over time or due to exposure to air or moisture. Further experiments were conducted by generating the Rulsalenlpyridine catalyst in situ as detailed below.

Example 18

Representative procedure for (1R,2R)-ethyl 2-(2,3-dihydrobenzofuran-4-yl)cyclopropanecarboxylate prepared using in situ generated Rulsalenlpyridine catalyst In a 3-neck neck round bottom flask fitted with a temperature probe, nitrogen inlet, magnetic stir bar and a septum was added (1R,2R)-(–)-1,2-cyclohexanediamino-N,N'-bis-(3,5-di-t-butylsalicylidene) (salen) and anhydrous THF. The resultant solution was cooled to 0-5° C. Lithium diisopropylamide(tetrahydrofuran) (1.5 M solution in cyclohexane; 2 equivalents) was added slowly at a rate that the reaction temperature was kept below 5° C. The solution was stirred for 1 hour at 0-5° C.

In a round bottom flask was charged dichloro(p-cymene)ruthenium(II) dimer (0.5 equivalents relative to the salen), pyridine (10 equivalents relative to the salen) and anhydrous THF. The mixture was stirred. The salen solution was added in one portion to the stirred suspension at ambient temperature. The salen reaction flask was rinsed with THF and the rinse solution was transferred to the round bottom flask. The resultant mixture was stirred overnight.

To a mixture of the in situ generated catalyst prepared in the previous paragraph was charged 4-vinyl-2,3-dihydrobenzofuran and toluene. To the stirred solution was added a solution of EDA in toluene. In some experiments, a second aliquot of EDA was charged. The solution was concentrated to remove the THF from the reaction solution. The residue was analyzed by in-process HPLC.

TABLE 2

Results of in situ Rulsalenlpyridine catalyst in the cyclopropanation of 4-vinyl-2,3-dihydrobenzofuran

| Exp. | Eq. Ru/Salen/pyr | Eq. EDA | Temp | Addition Time for EDA | % conversion of VBF to CPA[1] |
|---|---|---|---|---|---|
| 19 | 0.04 | 1.1 | 60° C. | Slow-overnight | 21% |
| 20 | 0.04 | 2.5 (First) | 60° C. | Rapid addition; | 50% (First) |
|  |  | 2.5 (Second) | 60° C. | $2^{nd}$ addition over 1 hour | 100% (Second) |
| 21 | 0.04 | 2.5 (First) | 60° C. | Slow 1 hour | 17% (First) |
|  |  | 2.5 (Second) | 60° C. | addition; $2^{nd}$ rapid addition over 7 min | 50% (Second) |
| 22 | 0.04 | 5 | 60° C. | Rapid addition over 9 minutes | 97% |

[1]CPA = (1R,2R)-ethyl 2-(2,3-dihydrobenzofuran-4-yl)cyclopropanecarboxylate

The results in Table 2 illustrate that the Ru/salen/pyridine catalyst generated in situ is active in the cyclopropanation reaction. Experiment 19 illustrates that the slow addition of ethyl diazoacetate (EDA) affords only a 21% yield of the product. Experiment 20 illustrates that rapid addition of 2.5 equivalents afforded a 50% conversion to product. When an additional 2.5 eq. of EDA was added over 1 h, the reaction went to 100% completion. Experiment 21 illustrates that the slow addition of 2.5 eq. of EDA over 1 h afforded only 17% conversion to product. Even after adding an additional 2.5 equivalents of EDA over 7 min. the reaction was still incomplete, with only a 50% conversion to product.

In experiment 22, 97% conversion was obtained using 5 equivalents of EDA with a rapid addition over 9 minutes. However, the need for a rapid addition of EDA to the reaction creates an unsafe operating condition especially on large scale such as in a pilot plant or manufacturing facility due to: (i) the build-up of EDA in the reactor; EDA is explosive and the reactor concentration of this reagent must be kept low; (ii) the rapid addition of EDA leads to an exothermic reaction that would be difficult to control; (iii) for each mole of EDA that is consumed, a mole of nitrogen is released; a rapid increase in the rate of the reaction in the presence of a high concentration of EDA could release a bulbous amount of nitrogen that may not be able to be effectively vented from the reactor, thus leading to a pressure build-up in the reactor and creating an unsafe condition; (iv) 5 equivalents of EDA were necessary to drive the reaction to completion; the use of such an excess of EDA creates an unsafe condition, requires the handling, transporting and storage of 4 times the amount of EDA than theoretically required in the reaction which is significant at manufacturing scale, requires extra monitoring to determine the fate of the excess EDA used in the reaction, and is inefficient. For at least these reasons, an alternative cyclopropanation catalyst and method was developed. In particular, conditions which gave high yields and stereoselectivity which utilized the alkenyl substrate as the limiting reagent and minimized the amount of the carbene precursor were developed.

It is therefore intended that the foregoing detailed description be regarded as illustrative rather than limiting, and that it be understood that it is the following claims, including all equivalents, that are intended to define the spirit and scope of this invention.

The invention claimed is:

1. A method of stereoselective cyclopropanation comprising the step of:
    combining a carbene precursor and an alkenyl substrate in the presence of a chiral catalyst to form a cyclopropyl product, the chiral catalyst is prepared in situ by the step of:
        combining an alkenyl ligand and a deprotonated chiral ligand in the presence of a ruthenium (II) metal;
    wherein the alkenyl ligand is of formula (I):

(I)

where $R^5$ is selected from the group consisting of hydrogen, $C_{1-8}$ alkyl, $C_{6-10}$ aryl, $C_{5-10}$ heteroaryl, $C_{3-10}$ heterocycle; and
where $R^6$ is selected from the group consisting of hydrogen, and $C_{1-8}$ alkyl; and
where $R^5$ and $R^6$ together with the atoms to which they are attached may form a carbocyclic ring;
wherein the deprotonated chiral ligand is of formula (III):

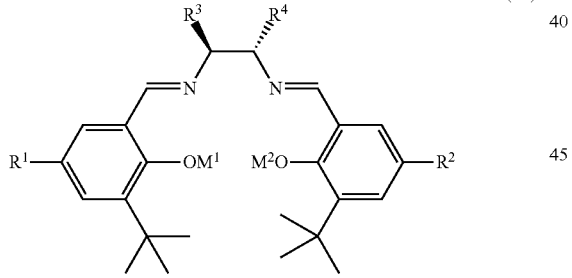
(III)

where $R^1$ and $R^2$ are each independently selected from the group consisting of hydrogen, substituted or unsubstituted $C_{1-8}$ alkyl, substituted or unsubstituted $C_{6-10}$ aryl, substituted or unsbstituted $C_{3-10}$ heterocyclyl, substituted or unsubstituted $C_{5-10}$ heteroaryl;
where $R^3$ and $R^4$ are each independently selected from the group consisting of substituted or unsubstituted $C_{1-8}$ alkyl, substituted or unsubstituted $C_{3-8}$ cycloalkyl, $C_{1-10}$ alkoxy, $C_{1-12}$ alkylamino, substituted or unsubstituted $C_{3-10}$ heterocyclyl, substituted or unsubstituted $C_{6-10}$ aryl, substituted or unsubstituted $C_{5-10}$ heteroaryl and substituted or unsubstituted arylalkyl; where $R^3$ and $R^4$ together with the atoms to which they are attached may form a ring; and
wherein $M^1$ and $M^2$ are each a counterion independently selected from the group consisting of Group I metal ions and Group II metal ions.

2. The method of claim 1, wherein the deprotonated chiral ligand is formed by deprotonating a chiral ligand of formula (III) where $M^1$ and $M^2$ are hydrogen with a base selected from the group consisting of metal alkoxides, metal amines, and metal alkyls, wherein the metal is selected from the group consisting of Group I or Group II metals.

3. The method of claim 1, wherein the alkenyl ligand is the same as the alkenyl substrate.

4. The method of claim 1, wherein the catalyst is prepared in the absence of an additive selected from the group consisting of a pyridyl donating ligand, a phosphorus donating ligand and a tertiary amine ligand.

5. The method of claim 3, wherein the carbene precursor is an alkyl diazoacetate.

6. The method of claim 5, wherein the cyclopropyl product is at least 90% trans.

7. The method of claim 1, wherein the molar amount of carbene precursor is greater than the molar amount of the alkenyl substrate.

8. The method of claim 1, wherein the deprotonated chiral ligand is of the formula:

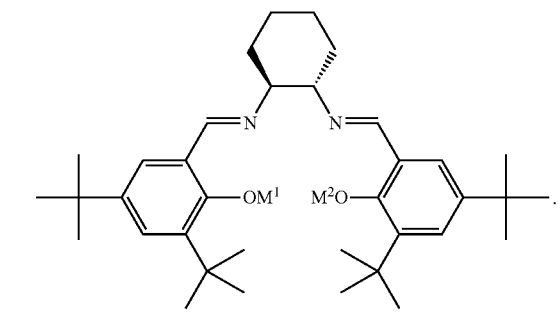

9. The method of claim 8, wherein the alkenyl ligand is selected from the group consisting of ethylene, cyclohexene, 1-hexene and 2,3-dihydro-4-vinylbenzofuran.

10. The method of claim 1, wherein the deprotonated chiral ligand is:

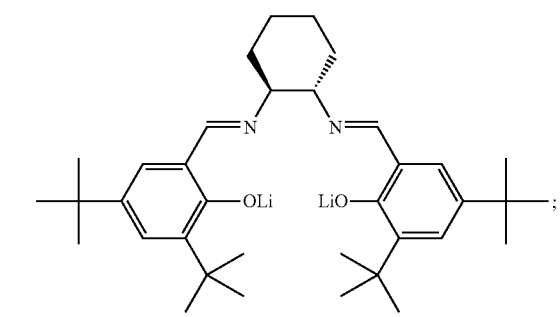

wherein each of the alkenyl ligand and the alkenyl substrate is

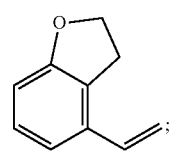

wherein the carbene precursor is ethyl diazoacetate; and wherein ruthenium (II) metal is [RuCl$_2$(p-cymene)]$_2$.

11. The method of claim 10, wherein the molar amount of carbene precursor is greater than the molar amount of the alkenyl substrate.

12. A method of stereoselective cyclopropanation consisting of the steps of:

combining an alkenyl ligand and a deprotonated chiral ligand in the presence of a ruthenium (II) metal to form a chiral catalyst in situ;

wherein the alkenyl ligand is of formula (I):

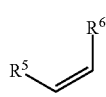
(I)

where R$^5$ is selected from the group consisting of hydrogen, C$_{1-8}$ alkyl, C$_{6-10}$ aryl, C$_{5-10}$ heteroaryl, C$_{3-10}$ heterocycle; and where R$^6$ is selected from the group consisting of hydrogen, and C$_{1-8}$ alkyl; and where R$^5$ and R$^6$ together with the atoms to which they are attached may form a carbocyclic ring;

wherein the deprotonated chiral ligand is of formula (III):

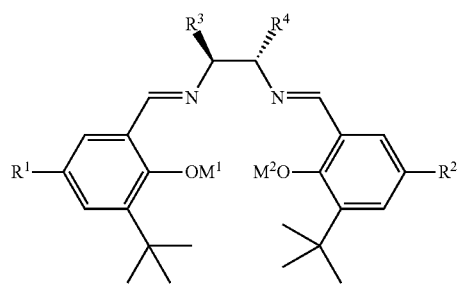
(III)

where R$^1$ and R$^2$ are each independently selected from the group consisting of hydrogen, substituted or unsubstituted C$_{1-8}$ alkyl, substituted or unsubstituted C$_{6-10}$ aryl, substituted or unsubstituted C$_{3-10}$ heterocyclyl, substituted or unsubstituted C$_{5-10}$ heteroaryl;

where R$^3$ and R$^4$ are each independently selected from the group consisting of subsituted or unsubstituted C$_{1-8}$ alkyl, substituted or unsubstituted C$_{3-8}$ cycloalkyl, C$_{1-10}$ alkoxy, C$_{1-12}$ alkylamino, substituted or unsubstituted C$_{3-10}$ heterocyclyl, substituted or unsubstituted C$_{6-10}$ aryl, substituted or unsubstituted C$_{5-10}$ heteroaryl and substituted or unsubstituted arylalkyl; where R$^3$ and R$^4$ together with the atoms to which they are attached may form a ring; and where M$^1$ and M$^2$ are each a counterion independently selected from the group consisting of Group I metal ions and Group II metal ions; and combining a carbene precursor and an alkenyl substrate in the presence of the chiral catalyst to form a cyclopropyl product.

13. In the stereoselective cyclopropanation of a carbene precursor and an alkenyl substrate with a chiral catalyst of the formulae (V) or (VI):

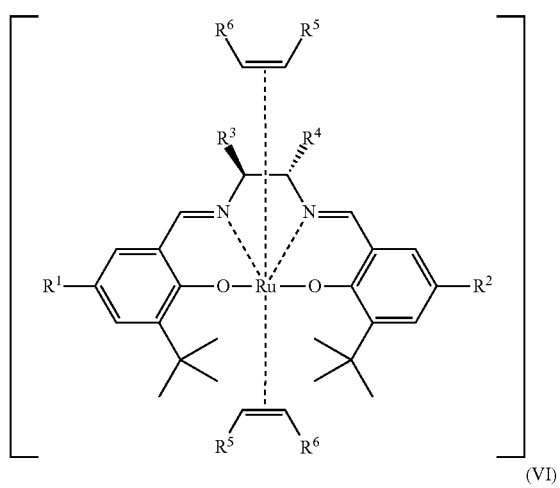
(V)

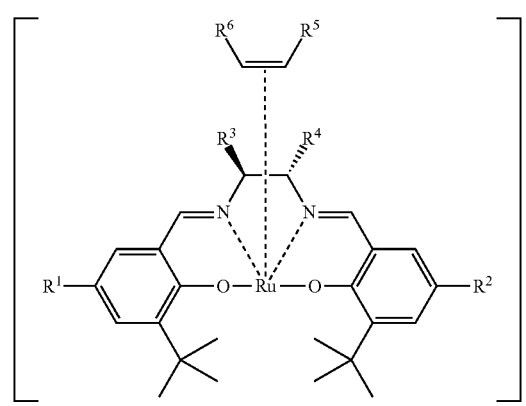
(VI)

where R$^5$ is selected from the group consisting of hydrogen, C$_{1-5}$ alkyl, C$_{6-10}$ aryl, C$_{5-10}$ heteroaryl, C$_{3-10}$ heterocycle; and where R6 is selected from the group consisting of hydrogen and C$_{1-8}$ alkyl; and where R$^5$ and R$^6$ together with the atoms to which they are attached may form a carbocyclic ring;

where R$^1$ and R$^2$ are each independently selected from the group consisting of hydrogen, substituted or unsubstituted C$_{1-8}$ alkyl, substituted or unsubstituted C$_{6-10}$ aryl, substituted or unsubstituted C$_{3-10}$ heterocyclyl, substituted or unsubstituted C$_{5-10}$ heteroaryl;

where R$^3$ and R$^4$ are each independently selected from the group consisting of substituted or unsubstituted C$_{1-8}$ alkyl, substituted or unsubstituted C$_{3-8}$ cycloalkyl, C$_{1-10}$ alkoxy, C$_{1-12}$ alkylamino, substituted or unsubstituted C$_{3-10}$ heterocyclyl, substituted or unsubstituted C$_{6-10}$ aryl, substituted or unsubstituted C$_{5-10}$ heteroaryl and substituted or unsubstituted arylalkyl;

where R$^3$ and R$^4$ together with the atoms to which they are attached may form a ring; and where M$^1$ and M$^2$ are each a counterion independently selected from the group consisting of Group I metal ions and Group II metal ions;

the improvement comprising generating the chiral catalyst in situ.

14. A catalyst for stereoselective reactions prepared by the step of combining an alkenyl ligand and a deprotonated chiral ligand in the presence of a ruthenium (II) metal;

wherein the alkenyl ligand is of formula (I):

(I)

where $R^5$ is selected from the group consisting of hydrogen, $C_{1-8}$ alkyl, $C_{6-10}$ aryl, $C_{5-10}$ heteroaryl, $C_{3-10}$ heterocycle; and
where $R^6$ is selected from the group consisting of hydrogen, and $C_{1-8}$ alkyl; and
where $R^5$ and $R^6$ together with the atoms to which they are attached may form a carbocyclic ring;
wherein the deprotonated chiral ligand is of formula (III):

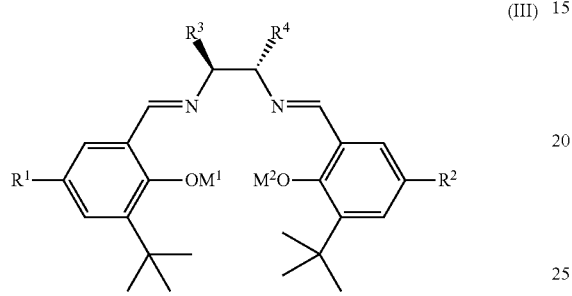
(III)

where $R^1$ and $R^2$ are each independently selected from the group consisting of hydrogen, substituted or unsubstituted $C_{1-8}$ alkyl, substituted or unsubstituted $C_{6-10}$ aryl, substituted or unsubstituted $C_{3-10}$ heterocyclyl, substituted or unsubstituted $C_{5-10}$ heteroaryl;
where $R^3$ and $R^4$ are each independently selected from the group consisting of subsituted or unsubstituted $C_{1-8}$ alkyl, substituted or unsubstituted $C_{3-8}$ cycloalkyl, $C_{1-10}$ alkoxy, $C_{1-12}$ alkylamino, substituted or unsubstituted $C_{3-10}$ heterocyclyl, substituted or unsubstituted $C_{6-10}$ aryl, substituted or unsubstituted $C_{5-10}$ heteroaryl and substituted or unsubstituted arylalkyl; where $R^3$ and $R^4$ together with the atoms to which they are attached may form a ring; and
where $M^1$ and $M^2$ are each a counterion independently selected from the group consisting of Group I metal ions and Group II metal ions.

15. The catalyst of claim 14, wherein the combining occurs in the absence of an additive selected from the group consisting of a pyridyl donating ligand, a phosphorus donating ligand and a tertiary amine ligand.

16. The catalyst of claim 14, wherein the alkenyl ligand is selected from the group consisting of ethylene, cyclohexene, 1-hexene and 2,3-dihydro-4-vinylbenzofuran.

* * * * *

UNITED STATES PATENT AND TRADEMARK OFFICE
CERTIFICATE OF CORRECTION

| | |
|---|---|
| PATENT NO. | : 8,558,017 B2 |
| APPLICATION NO. | : 13/316729 |
| DATED | : October 15, 2013 |
| INVENTOR(S) | : Pereira et al. |

It is certified that error appears in the above-identified patent and that said Letters Patent is hereby corrected as shown below:

In the Specifications

Column 3, line 45

Delete: "$C_{1-6}$ alkyl"

Insert: -- $C_{1-8}$ alkyl --

Column 3, line 65

Delete: "$C_{1-6}$ alkyl"

Insert: -- $C_{1-8}$ alkyl --

Column 4, line 4

Delete: "$C_{10}$ heterocyclyl"

Insert: -- $C_{3-10}$ heterocyclyl --

Column 4, line 55

Delete: "$C_{1-6}$ alkyl"

Insert: -- $C_{1-8}$ alkyl --

Signed and Sealed this
Twenty-fifth Day of February, 2014

Michelle K. Lee
*Deputy Director of the United States Patent and Trademark Office*

CERTIFICATE OF CORRECTION (continued)
U.S. Pat. No. 8,558,017 B2

Column 4, line 63

Delete: "unsubstituted $C_{3-6}$"

Insert: -- unsubstituted $C_{3-8}$ --

Column 10, line 31

Delete: "$C_{1-10}$ aryl"

Insert: -- $C_{6-10}$ aryl --